US00PP12888P2

(12) United States Plant Patent
Trees

(10) Patent No.: US PP12,888 P2
(45) Date of Patent: Aug. 27, 2002

(54) VERBENA PLANT NAMED 'BALWILAPI'

(75) Inventor: Scott Trees, Shell Beach, CA (US)

(73) Assignee: Ball Floraplant, a division of Ball Horticultural Company, West Chicago, IL (US)

( * ) Notice: Subject to any disclaimer, the term of this patent is extended or adjusted under 35 U.S.C. 154(b) by 0 days.

(21) Appl. No.: 09/822,611

(22) Filed: Mar. 30, 2001

(51) Int. Cl.[7] ..... A01H 5/00
(52) U.S. Cl. ..... Plt./308
(58) Field of Search ..... Plt./308

*Primary Examiner*—Bruce R. Campell
*Assistant Examiner*—Kent L. Bell
(74) *Attorney, Agent, or Firm*—Gardner Carton & Douglas

(57) ABSTRACT

A new and distinct Verbena plant named 'Balwilapi', characterized by its lavender pink flowers, mounded trailing habit, and dark green leaves.

2 Drawing Sheets

LATIN NAME OF GENUS AND SPECIES OF PLANT CLAIMED

*Verbena hybrida.*

VARIETY DENOMINATION

'Balwilapi'.

BACKGROUND OF THE INVENTION

The present invention comprises a new and distinct verbena plant, botanically known as *Verbena hybrida*, and hereinafter referred to by the cultivar name 'Balwilapi'.

The new cultivar was developed by the inventor through a controlled breeding program during 1998, at Arroyo Grande, Calif. The objective of breeding program was the development of verbena cultivars with semi-trailing mounded habit, continuous flowering, excellent basal branching and small dark green foliage.

The female (seed) parent of 'Balwilapi' was the commercially available verbena 'Quartz Blue' (not patented), which exhibits dark purple flowers, upright growth habit and medium green foliage. The male (pollen) parent of 'Balwilapi' was 'Temari Violet' (not patented), which exhibits dark lavender flowers, a trailing growth habit and medium green foliage.

Asexual reproduction of the new cultivar by terminal stem cuttings in Arroyo Grande, Calif. and West Chicago, Ill. has demonstrated that the characteristics of the new cultivar as herein described are firmly fixed and are retained through successive generations of such asexual propagation.

SUMMARY OF THE INVENTION

It was found that the cultivar of the present invention:

(a) Exhibits lavender pink flowers, (b) Forms dark green foliage, (c) Exhibits a good basal branching character and (d) Exhibits a mounded and trailing growth habit.

When the new cultivar of the present invention is compared to its male parent, 'Temari Violet', it is found that the new cultivar has larger leaves, more flowers per inflorescence and darker flower color as detailed in TABLE A.

When the new cultivar of the present invention is compared to 'Balazlavi' (co-pending U.S. Plant patent application Ser. No. 09/808,318), the new cultivar is distinguished from 'Balazlavi' primarily in petal coloration. When the new cultivar of the present invention is compared to 'Balazdapi' (co-pending U.S. Plant patent application Ser. No. 09/808,204), the new cultivar is distinguished from 'Balazdapi' primarily in petal coloration.

BRIEF DESCRIPTION OF THE PHOTOGRAPH

The accompanying photographs illustrate the overall appearance of the new cultivar as true as it is reasonably possible to obtain colored reproductions of this type. Color in the photographs may differ slightly from the color values cited in the detailed botanical description which accurately describe the actual colors of the new Verbena.

Sheet 1 depicts the growth habit of 'Balwilapi' in a garden setting with four plants in a five-gallon container.

Sheet 2 depicts a side perspective view of three plants of 'Balwilapi'. The plants were grown in a greenhouse in West Chicago, Ill., U.S.A.

DETAILED BOTANICAL DESCRIPTION

The 'Balwilapi' cultivar has not been observed under all possible environmental conditions to date. Accordingly, it is possible that the phenotype may vary somewhat with variations in the environment, such as temperature, light intensity, and day length.

The chart used in the identification of colors described herein is The R.H.S. Colour Chart of The Royal Horticultural Society, London, England. The color values were determined on Aug. 15, 2000. The readings were taken between 1:00 and 3:00 p.m. under natural daylight conditions. The plants used for the descriptions were produced from cuttings taken from stock plants and grown about 11 weeks after planting rooted cuttings in 10 cm pots in a double poly carbonate covered greenhouse in West Chicago, Ill. under conditions comparable to those used in commercial practice while utilizing a soilless growth medium and maintaining temperatures of approximately 72° F. during the day and approximately 65° F. during the night.

Classification:

*Botanical.*—*Verbena hybrida* cultivar 'Balwilapi'.

Parentage:

*Female parent.*—'Quartz Blue'.

*Male parent.*—'Temari Violet'.

Propagation:

*Type cutting.*—Terminal tip.

*Time to initiate roots.*—Approximately 14–21 days with the shorter times generally being experienced in the summer and the longer times in the winter.

*Root description.*—Fibrous, branching.

Plant description:

*Habit of growth.*—Moderately vigorous with good basal branching. Pinching improves basal branching. A mature plant, 8–9 weeks after the planting of a rooted cutting, commonly measures approximately 29.8 cm in height and approximately 33 cm in width.

*Form.*—Mounded and trailing.

*Stem.*—Tetagonal, approximately 1.6 mm in diameter, with moderate pubescence, 146B with no anthocyanin pigmentation. Internode length is approximately 2 cm.

*Foliage.*—Leaves are opposite, ovate with serrate margin, acute apex, base is attenuate to oblique. Texture: Velvety, covered with dense short hairs on upper surface and along veins on lower surface. Size: Approximately 3.8 cm in length and approximately 2.1 cm at widest point. Color: Upper surface is 139A, lower surface is 137B. Venation: Reticulate and 144D on both surfaces. Petiole: Approximately 6 mm in length, 144C.

Flowering description:

*Flowering habit.*—Freely flowering.

*Natural flowering season.*—Spring through autumn.

*Inflorescence type.*—Corymb. Approximately 4 cm deep and approximately 5.3 cm in diameter with approximately 19 fully open flowers per inflorescence at any one time.

*Peduncle.*—Approximately 5.3 cm in length, 2 mm in diameter.

*Petals.*—Five, fused at base, non-overlapping, flat.

*Flower.*—Diameter: Approximately 2 cm. Corolla tube: Approximately 2.1 cm long, 150D.

*Calyx.*—1.3 cm in length, 2 mm in diameter, 5 toothed, 5 ribbed, with stipules. Color: Ribs and stipules are 143A with 144D between the ribs (both surfaces).

*Flower color.*—Upper surface, fully opened: Between 82A and 82B with streaks of 83B. Color is 155D near the base and changes to 154C just at the opening of the corolla tube. Whiskers of 2D surround the opening of corolla tube. Lower surface, fully opened: Between 85A and 85B.

*Reproductive organs.*—There are 4 stamens and one pistil 2 cm in length. Pollen color is 5C.

*Seed production.*—Seed production has not been observed.

*Disease resistance.*—Resistance to common diseases of verbena has not been observed.

TABLE A

| CHARACTERISTIC | 'BALWILAPI' | 'TEMARI VIOLET' |
|---|---|---|
| LEAF LENGTH × LEAF WIDTH-CM | 3.8 × 2.1 | 2 × 1.4 |
| PETIOLE LENGTH-MM | 6 | 3 |
| INFLORESCENCE DEPTH × WIDTH-CM | 4 × 5.3 | 2.9 × 4.3 |
| #FLOWERS PER INFLORESCENCE | 19 | 16 |
| FLOWER COLOR-UPPER SURFACE-RHS | BETWEEN 82A AND 82B WITH STREAKS OF 83B | BETWEEN 80A & 81A |

I claim:

1. A new and distinct cultivar of *Verbena hybrida* plant named 'Balwilapi' substantially as herein shown and described, which:

(a) Exhibits lavender pink flowers, (b) Forms dark green foliage, (c) Exhibits a good basal branching character and exhibits a mounded and trailing growth habit.

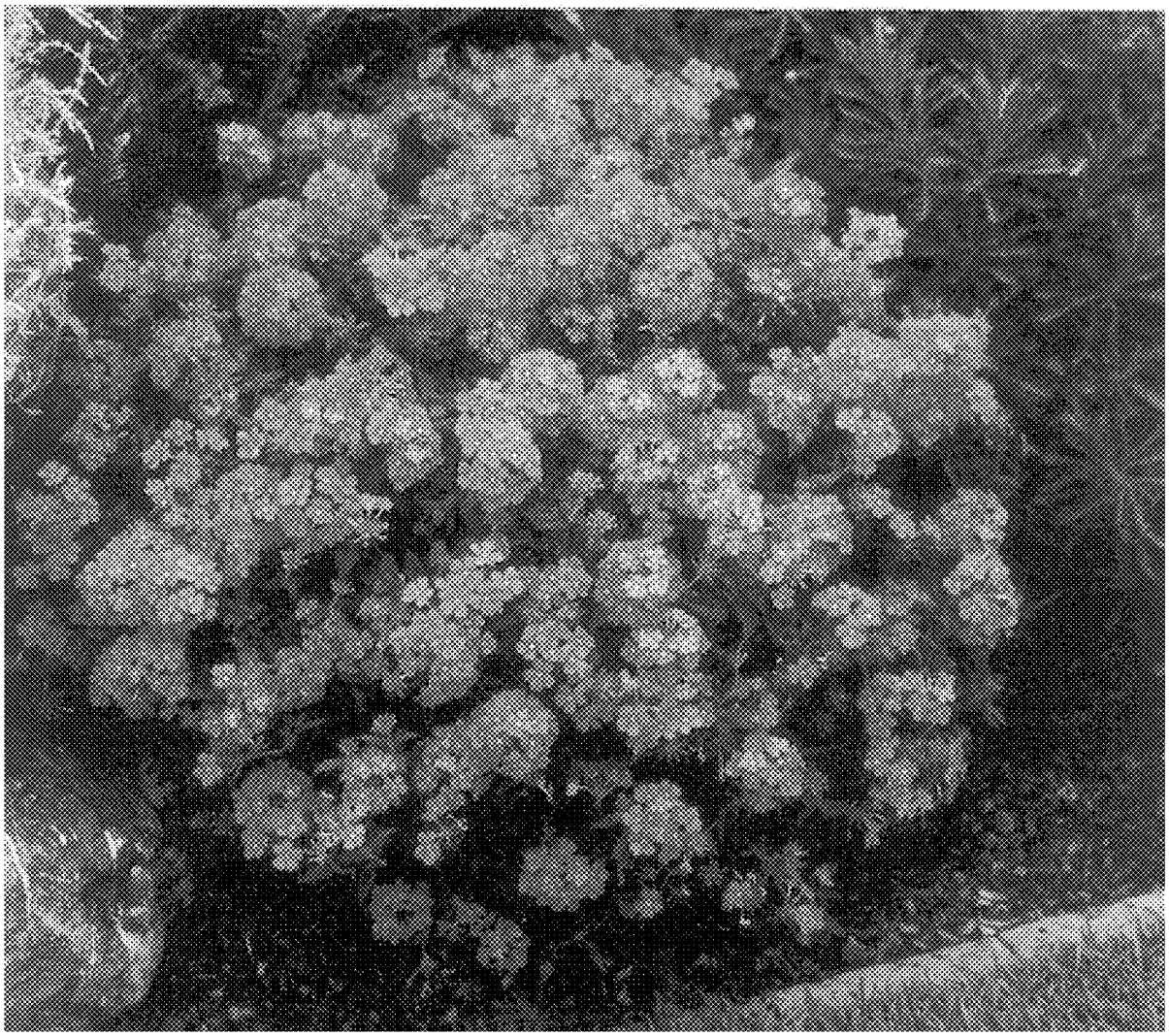

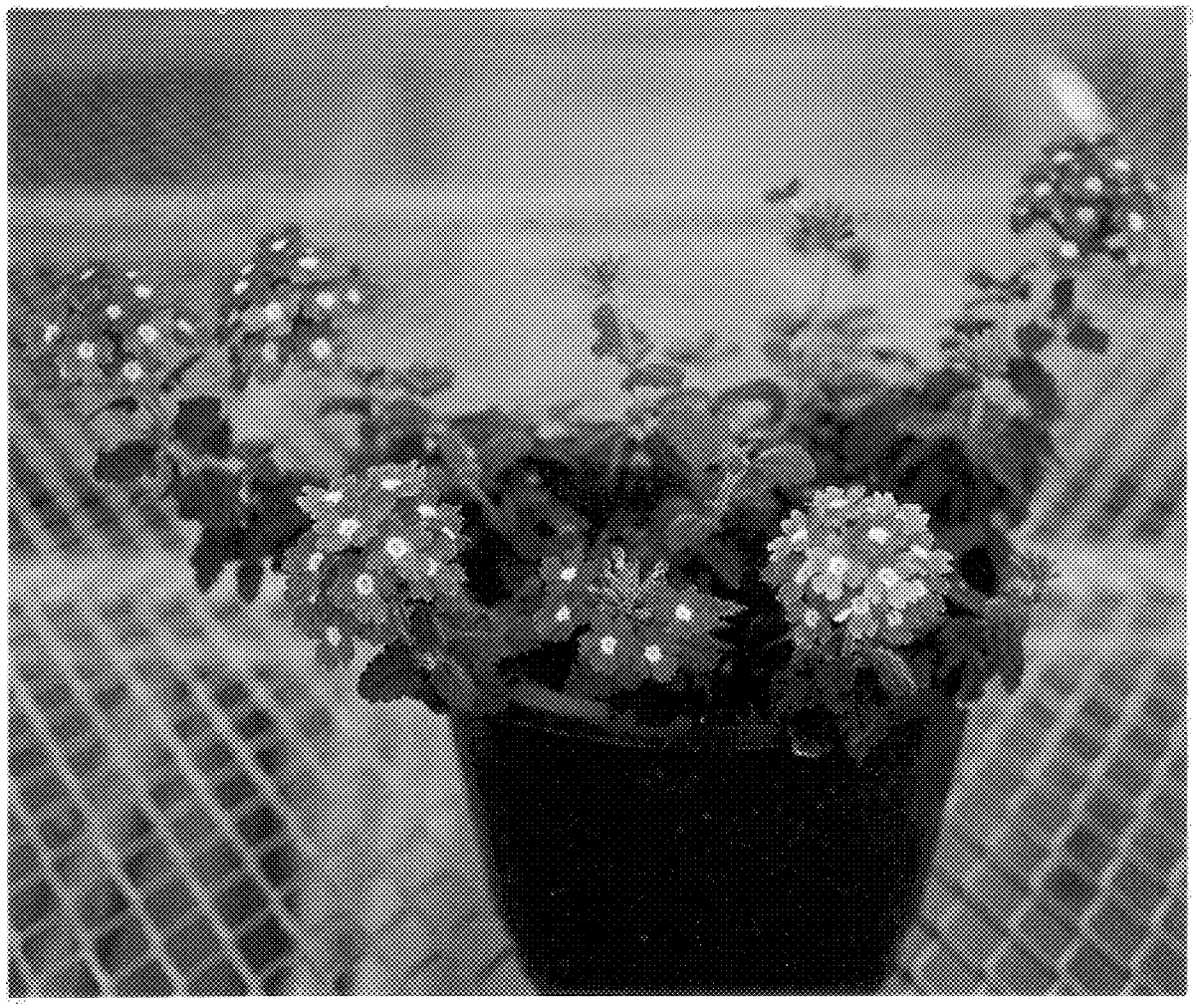

* * * * *